United States Patent [19]

Fields et al.

[11] 4,117,111

[45] Sep. 26, 1978

[54] METHOD FOR LOWERING BLOOD CHOLESTEROL LEVEL

[75] Inventors: Joseph E. Fields, Ballwin; John H. Johnson, Kirkwood, both of Mo.

[73] Assignee: Monsanto Company, St. Louis, Mo.

[21] Appl. No.: 572,799

[22] Filed: Apr. 29, 1975

Related U.S. Application Data

[60] Division of Ser. No. 353,832, Apr. 23, 1973, Pat. No. 3,923,972, which is a continuation-in-part of Ser. No. 188,577, Oct. 12, 1971, abandoned, which is a continuation-in-part of Ser. No. 789,081, Jan. 2, 1969, abandoned.

[51] Int. Cl.$^2$ .............................................. A61K 31/74
[52] U.S. Cl. ............................................................ 424/78
[58] Field of Search ................................................ 424/78

[56] References Cited

U.S. PATENT DOCUMENTS

| | | | |
|---|---|---|---|
| 3,224,941 | 12/1965 | Nash et al. | 424/78 |
| 3,308,020 | 3/1967 | Wolf et al. | 424/78 |
| 3,655,869 | 4/1972 | Wharton et al. | 424/78 |
| 3,749,771 | 7/1973 | Regelson et al. | 424/78 |

FOREIGN PATENT DOCUMENTS 664,326  6/1963  Canada .................................. 424/78

*Primary Examiner*—Frederick E. Waddell
*Attorney, Agent, or Firm*—Joseph D. Kennedy; John D. Upham

[57] ABSTRACT

The level of blood cholesterol in a living animal body in which a state of hypercholesterolemia exists is lowered by orally administering to said animal body a pharmaceutically effective amount of a polymer, which is (1) polymerized unsaturated carboxylic acid or anhydride, or (2) a copolymer of (a) an unsaturated monomer having, for Example, 2 to 30 carbon atoms and, (b) an unsaturated carboxylic acid, anhydride or derivative thereof as exemplified by octadecene-1/maleic anhydride copolymer. Polymers having lipophilic properties are a preferred class. A typical dosage is an amount which represents in the range of from about 0.01 to about 5.0% of the diet.

23 Claims, No Drawings

METHOD FOR LOWERING BLOOD CHOLESTEROL LEVEL

REFERENCE TO RELATED APPLICATIONS

This application is a division of our copending application Ser. No. 353,832, filed Apr. 23, 1973, now U.S. Pat. 3,923,972 which in turn is a continuation-in-part of our copending application Ser. No. 188,577, filed Oct. 12, 1971, now abandoned, which, in turn is a continuation-in-part of our copending application Ser. No. 789,081, now abandoned, filed Jan. 2, 1969.

BACKGROUND OF THE INVENTION

This invention relates to a method for lowering the blood cholesterol level in a living animal body, in which a state of hypercholesterolemia exists. In a particular aspect this invention relates to a method for lowering the blood cholesterol level in a living animal body in which a state of hypercholesterolemia exists by orally administering to the living animal body a pharmaceutically effective amount of a polymer selected from the group consisting of (1) polymerized unsaturated carboxylic acid or anhydride and (2) a copolymer of (a) an unsaturated monomer having, for example, 2 to 30 carbon atoms, such as, alkene, alkylcarboxyalkene, phenylalkene, and alkoxyalkene and, (b) an unsaturated carboxylic acid, anhydride or derivative thereof.

The link between high levels of blood cholesterol (hypercholesterolemia) and cardio-vascular disease in warmblooded vertebrates is well established. The malady is known not only to contribute to chronic conditions of high blood pressure, but to increase the risk of incapacitating and often fatal coronary attacks.

SUMMARY OF THE INVENTION

It is an object of the present invention to provide a method for lowering the blood cholesterol in a living animal body in which a state of hypercholesterolemia exists.

It is a further object of the present invention to provide compositions which are effective in the aforesaid method in lowering blood cholesterol levels in a living animal body in which a state of hypercholesterolemia exits.

Other objects and advantages of the present invention will be apparent from the specification and appended claims.

The present invention resides in the discovery that the level of blood cholesterol in a living animal body in which a state of hypercholesterolemia exists is lowered by orally administering to said animal body a pharmaceutically effective amount of a polymer selected from the group consisting of (1) a polymerized unsaturated carboxylic acid, or anhydride (2) a copolymer of (a) an unsaturated monomer having, for example, 2 to 30 carbon atoms, and (b) an unsaturated carboxylic acid, anhydride or derivative thereof. By this method the blood cholesterol level in living animal bodies, including warm-blooded vertebrate animals, such as chickens, dogs, cats, cattle, swine and primates, for example monkeys, is effectively lowered.

DETAILED DESCRIPTION

The polymer can be orally administered to the living animal body by any suitable means, and in any suitable form. For example, the polymer can be incorporated into ordinary foodstuffs and beverages containing nutritional values in an amount sufficient to produce the desired reduction of blood cholesterol. Also, the polymer can be incorporated into a pharmaceutical composition of the form customarily employed for oral administration. Pharmaceutical compositions containing the polymer may be in liquid form, for example, a solution or suspension specifically adapted for oral administration or in solid form, for example, a tablet, capsule, pill or packaged powder. Advantageously, the pharmaceutical composition containing the polymer can be prepared in unit dosage form using pharmaceutically acceptable carriers, such as, for example, starch, glucose, lactose, gelatin, sucrose, etc. and the like. If desired, the dosage unit can be made up in a sustained release form to give a controlled dosage over an extended period of time.

The amount or dosage of polymer administered to the living animal body will, of course, vary depending among other things, on the size of the living animal body, the particular living animal body to be treated, the level of blood cholesterol, and the general health of the living animal body, and any pharmaceutically effective amount may be employed. The dosage can be determined with regard to established medical practice. Generally the amount of polymer administered on a daily basis is in the range of from about 0.01 to about 5.0% of the total diet, and typically in the range of from about 0.05 to about 3.0%.

The polymer of use in the present invention may be water soluble or water-insoluble. Many of the normally water-soluble polymers are converted to the water-insoluble form by introduction of sufficient crosslinks in the known manner. Crosslinking may be accomplished either during the preparation of the polymer or by subsequent treatment of the polymer to make the polymer insoluble in water. The water insolubility of the polymer can be varied by regulation of the degree of crosslinking of the polymer. The term "water-insoluble" as used herein is taken to mean that the polymer concerned does not dissolve in water or aqueous solutions, even though it may have such characteristics as a high degree of swelling, due to solvation by water even to the extent of existence in a gel form. Such characteristics are typically imparted by crosslinking.

As previously indicated, the polymers employed in the method of the present invention, are (1) polymerized unsaturated carboxylic acids or anhydrides, (2) copolymers of (a) an unsaturated monomer having, for example, 2 to 30 carbon atoms, and (b) an unsaturated carboxylic acid anhydride or unsaturated carboxylic acid derivative, preferably having a weight average molecular weight of at least 1,000 and a degree of polymerization of at least 8.

The polymer may advantageously be an EMA-type polymer.

Among the EMA-type polymers suitable for the practice of the instant invention are polymers and pharmaceutically acceptable salts of polymers having units of the formula

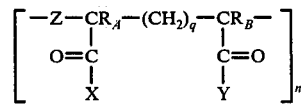

wherein: $R_A$ and $R_B$ are selected from the group consisting of hydrogen, halogen (preferably chlorine), alkyl of 1 to 4 carbon atoms (preferably methyl), cyano, phenyl, or mixtures thereof; provided that not more than one of $R_A$ and $R_B$ is phenyl; Z is a bivalent radical (preferably alkylene, phenylalkylene, alkoxyalkylene, alkylcarboxyalkylene and aliphatic acyloxyalkylene) of 1 to 30 carbon atoms, q is zero or one, X and Y are selected from hydroxy, —O alkali metal, OR, —OH—NH$_3$, —OH—R$_3$N, —OH—R$_2$NH, —OH—RNH$_2$, —NRR', —(Q)$_p$—W—(NR'R')$_x$ and —(Q)$_p$—W—(—OH)$_x$, wherein x is 1 to 4 and p is zero or one, wherein R is selected from the group consisting of hydrogen, alkyl, phenylakyl, or phenyl, in each case of 1 to 18 carbon atoms, wherein R' is H or R, wherein Q is oxygen or —NR'—, and wherein W is a bivalent radical preferably selected from alkylene, phenylene, alkylene amine and phenylalkylene having up to 20 carbon atoms, X and Y taken together can be oxygen or —NR—, —N—W—(NR'R')$_x$ or —N—W—(NR'R'R")$_x$+ wherein R, W, R' have the meanings previously assigned and R" is alkyl of 1 to 18 carbon atoms, benzyl or aromatic-substituted benzyl. The units of the formula given above are recurring n being at least 8 and can be as much as 100,000 degrees of polymerization. When the units are recurring the symbols in the various recurring units do not necessarily stand for the same thing in all of the recurring units.

Many of these polymers suitable for the practice of the present invention or suitable after conversion to derivatives are commercially available.

The polycarboxylic acid polymers can be of the non-vicinal-type including those containing monomer units, such as acrylic acid, acrylic anhydride, methacrylic acid, crotonic acid or their respective derivatives, including partial salts, amides and esters or of the vicinal type, including maleic, itaconic, citraconic, a-dimethyl maleic, a-butyl maleic, a-phenyl maleic, fumaric, aconitic, a-chloromaleic, a-bromomaleic, a-cyanomaleic acids including their salts, amides and esters. Anhydrides of the foregoing acids are also advantageously employed.

Co-monomers suitable for use with the above polycarboxylic acid monomers include a-olefins, such as ethylene, 2-methyl-pentene-1, propylene, butylene, 1-or 2-butene, 1-hexene, 1-octene, 1-decene, 1-dodecene, 1-octadecene, and other vinyl monomers, such as styrene, a-methyl styrene, vinyltoluene, vinyl acetate, vinyl chloride, vinyl formate, vinyl alkyl ethers, e.g. methylvinylether, alkyl acrylates, alkyl methacrylates, acrylamides, methacrylamides, alkylmethacrylamides and alkylacrylamides, or mixtures of these monomers. Reactivity of some functional groups in the copolymers resulting from some of these monomers permits formation of other useful functional groups in the formed copolymer, including hydroxy, lactone, amine and lactam groups.

Any of the said carboxylic acids or derivatives, may be copolymerized with any of the other monomers described above, and any other monomer which forms a copolymer with carboxylic acids or derivatives. Although these copolymers can be prepared by direct polymerization of the various monomers, frequently they are more easily prepared by an after-reaction modification of an existing copolymer. Copolymers are conveniently identified in terms of their monomeric constituents. The names so applied refer to the molecular structure and are not limited to the polymers prepared by the copolymerization of the specified monomers.

The initial copolymers of anhydrides and another monomer can be converted to carboxyl-containing copolymers by reaction with water, and to ammonium, alkali and alkaline earth metal and alkylamine salts thereof by reaction with alkali metal compounds, alkaline earth metal compounds, amines or ammonia. Other suitable derivatives of the above polymers include the alkyl or other esters and amides, alkyl amides, dialkyl amides, phenylalkyl amides or phenyl amides prepared by reacting carboxyl groups on the polymer chain with the selected amines or alkyl or phenylalkyl alcohol, as well as amino esters, amino amides, hydroxy amides and hydroxy esters, wherein the functional groups are separated by alkylene, phenyl, alkylene amine, alkylene oxide, phenylalkyl, phenylalkylphenyl, or alkylphenylalkyl or other aryl groups. Moieties bearing amine or amine salts including quaternary salt groups are conveniently formed by reaction of the carboxyls of their anhydride precursors, where applicable with polyfunctional amines such as dimethylaminopropylamine or dialkylaminoalcohols such as dimethylaminoethanol, the former forming an amide linkage with the polymer, or in certain cases at higher temperatures forming an imide linkage with vicinal carboxyls, and the latter forming an ester linkage. Such pendant free amine groups can then be converted, if desired, to their simple or quaternary salts.

Polymers of the above type include the following classes of polymers, and their derivatives: ethylene/maleic anhydride copolymers, isobutylene/maleic anhydride copolymer, 2-methyl-pentene-1/maleic anhydride copolymers, styrene/maleic anhydride copolymers, vinylacetate/maleic anhydride copolymers, a-methylstyrene/maleic anhydride copolymers, polymaleic anhydride polymers, polyacrylic anhydride polymers, polyacrylic acid polymers, octadecene-1/maleic anhydride copolymers, loweralkylaminoloweralkylimide of octadecene-1/maleic anhydride copolymers, aliphatic ester of ethylene/maleic anhydride copolymers, vinylalkylether/maleic anhydride copolymers, aliphatic methacrylate/methacrylamide copolymers, aliphatic methacrylate/diloweralkylaminoloweralkyl methacrylic copolymers, loweralkylaminoloweralkylimide of styrene maleic anhydride copolymers and polymethacrylic acid polymers.

Individual examples of such polymers include ethylene/maleic anhydride copolymer, the disodium salt of isobutylene/maleic anhydride copolymer, the calcium salt of styrene/maleic anhydride copolymer, hydrolyzed propylene/maleic anhydride copolymer, the monopotassium salt of divinylether/maleic anhydride copolymer, hydrolyzed vinyl methyl ether/citraconic anhydride copolymer, half lauryl ester of octene-1/maleic anhydride copolymer, octadecene-1/maleic anhydride copolymer, ethylene/maleic acid copolymer, the dipotassium salt of isobutylene/maleic acid copolymer, the half amide half ammonium salt of isobutylene/maleic anhydride copolymer, ethylene/acrylic acid copolymer, ethylene/acrylic anhydride copolymer, half capryl ester of hexene-1/acrylic anhydride copolymer, ethylene/aconitic anhydride copolymer, half ethylamide of styrene/maleic anhydride copolymer, ethylene/fumaric acid copolymer, octylamide acid of ethylene/maleic anhydride copolymer, octadecylamide ammonium salt of vinylmethylether/maleic anhydride copolymer, dimethylaminopropylamide acid of divinylether/maleic anhydride copolymer, isobutylamide of vinyl acetate/maleic anhydride copolymer, methiodide quaternary derivative of N, N-dimethylaminoethylamide of polymaleic anhydride, octadecyl ester ammonium salt of ethylene/itaconic anhydride copolymers, butylamine half amide of hexene-1/chloromaleic anhydride copolymer, the partial diamide of ethylene/maleic anhydride copolymer, n-decylamide of decene-1/maleic anhydride copolymer, N, N-diethylaminopropylamide ammonium salt of isobutylene/maleic anhydride copolymer, dimethyl sulfate quaternary salt of dimethylaminoethylamide of polymaleic anhydride, the partial half hexylamide of vinylmethylether/maleic anhydride copolymer, the diammonium salt of ethylene/maleic anhydride copolymer, the monoamide acid of propylene/maleic anhydride copolymer, N-ethyl monoamide of divinylether/maleic anhydride copolymer, N-dodecyl monoamide of vinylmethylether/maleic anhydride copolymer, N, N-dimethylaminopropylimide of triacontene/maleic anhydride copolymer, N, N-dimethylaminopropyl monoamide of styrene/citraconic anhydride copolymer, n-butyl-monoamide of polymaleic anhydride, N, N-diethylmonoamide ammonium salt of vinyl acetate/maleic anhydride copolymer, n-butylimide of ethylene/maleic anhydride copolymer, octadecylimide of polymaleic anhydride, N, N-dimethylaminopropylimide of styrene/maleic anhydride copolymer, dimethylsulfate quaternary salt of diethylaminopropylimide of divinylether/maleic anhydride copolymer, N, N-dimethylaminopropyl half amide of paramethyl styrene/-maleic anhydride copolymer, methyliodide quaternary salt of dimethylaminohexyl half amide half ammonium salt of a-methylstyrene/maleic anhydride copolymer, N, N-diethylaminoethyl half amide half sodium salt of isobutylene/maleic anhydride copolymer, partial lauryl ester of ethylene/maleic anhydride copolymer, vinyl octadecyl ether/maleic anhydride copolymer, stearyl methacrylate/methacrylamide copolymer and stearyl methacrylate/N,N-dimethylaminoethyl methacrylate copolymer.

A particularly preferred class of polymers for use in the present invention are lipophilic polymers, that is, polymers which have a lipophilic grouping or groupings included therein. A lipophilic grouping or moiety typically contains 6 or more atom units and may be in any suitable form such as a polyalkylene or alkylene oxide containing 6 or more atom units or as an ester, amide or imide unit containing 6 or more atom units, for example, 6 to 30 carbon atoms formed by reaction of the carboxyl containing monomer with lipophilic amines or alcohols such as, for example, hexanol, octanol, octylamine, hexylamine, octadecanol, etc. and the like. Examples of such preferred polymers include the octadecylimide of polymaleic anhydride, the methyl iodide quaternary salt of dimethylaminohexyl half amide half ammonium salt of a-methylstyrene/maleic anhydride copolymer, dodecyl monoamide of vinylmethylether/-maleic anhydride copolymer, the octadecyl ester ammonium salt of ethylene/itaconic anhydride copolymer, the decylamide of decene-1/maleic anhydride copolymer, octadecene-1/maleic anhydride copolymer etc. and the like.

Pharmaceutically acceptable alkaline earth metals and alkali metals, such as calcium, magnesium and potassium are useful in preparing conveniently administered forms of the polyelectrolyte polymers of this invention. The salts of metals such as magnesium, aluminum, zinc, iron, barium and bismuth are also useful in the present invention.

Representative EMA-type carboxylic acid or anhydride-olefin polymers, especially maleic acid or anhydride-olefin polymers of the foregoing type are known, for example, from U.S. Pat. Nos. 2,378,629; 2,396,785; 3,157,595; and 3,340,680. Generally, the copolymers are prepared by reacting ethylene or other unsaturated monomer, or mixtures thereof, with the acid anhydride in the presence of a peroxide catalyst in an aliphatic or aromatic hydrocarbon solvent for the monomers but nonsolvent for the interpolymer formed. Suitable solvents include benzene, toluene, xylene, chlorinated benzene and the like. While benzoyl peroxide is usually the preferred catalyst, other peroxides such as acetyl peroxide, butyryl peroxide, ditertiary butyl peroxide, lauroyl peroxide and the like, or any of the numerous azo catalysts, are satisfactory since they are soluble in organic solvents. The copolymer typically contains from about 25 to about 75% (mole %) of the olefin and preferably contains substantially equimolar quantities of the olefin residue and the anhydride or acid residue; that is, a mole ratio of olefin to anhydride or acid in the range of from about 2:3 to about 3:2. Generally, the copolymer will have a degree of polymerization of 8 to 100,000 preferably about 100 to 5,000, and a molecular weight of about 1,000 to 1,000,000, preferably about 10,000 to 500,000. The properties of the polymer, such as molecular weight, for example, are regulated by proper choice of the catalyst and control of one or more of the variables such as ratio of reactants, temperature, and catalyst concentration or the addition of regulating chain transfer agents, such as diisopropyl benzene, propionic acid, alkyl aldehydes, or the like. Numerous of these polymers are commercially available.

Derivatives containing basic or cationic groups can be prepared by any convenient procedure. Representative derivatives of polymers employed in the present invention are known to the art, for example, from U.S. Pat. 3,398,092. One group of useful derivatives are those in which the carboxyl groups are partially replaced with basic or cationic bearing moieties. For example, useful derivatives are conveniently formed by reaction of the carboxyls with polyfunctional amines such as dimethylaminopropylamine or dialkylaminoalcohols such as dimethylaminoethanol, the former forming an amide linkage with the polymer, or in certain cases at higher temperatures forming an imide linkage with the vicinal carboxyls and the latter forming an ester linkage. Such pendant free amine groups can then be converted, if desired, to their simple or quaternary salts.

Imides of a starting carboxyl or carboxylic acid anhydride containing polymer, e.g., EMA, are produced by:

(A) Heating a limiting amount of a secondary or tertiary aminoloweralkylamine with the anhydride or carboxyl-containing form of the polymer in a suitable solvent (e.g. Xylene) at a temperature of about 140°-150° C. until water is no longer given off. Such a reaction simultaneously results in formation of imide groups in proportion to the amount of amine added and in the reformation of anhydride groups for the remainder of the polymer units. In this manner, imide-polymer products are formed which possess imide linkages, the remaining carboxyl groups, when present, being in the anhydride form.

(B) Alternatively, a partial amidepolymer product may be converted to the partial imide polymer product by heating a partial amide-polymer product in vacuo at 140°-150° C. until water is not longer given off. Such an imide polymer product likewise possesses comparable proportions of imide and anhydride groups depending upon the number of amide groups originally contained in the starting partial amide-polymer product.

Partial secondary or tertiary aminoloweralkylamides of the starting carboxyl or carboxylic acid anhydride-containing polymer, e.g., EMA, are obtained by contacting the polymer with a limiting amount of the selected amine in suspension in a solvent such as benzene or hexane, resulting in formation of a partial amide-acid-anhydride derivative of the polymer, or a corresponding amidecarboxylate derivative thereof. The number of amide groups is dependent upon the quantity of the amine used as compared with the quantity of polymer employed.

Partial aminoester-polymer products are most conveniently prepared by heating at reflux temperatures overnight a limiting quantity of the selected aminoalcohol and carboxyl or carboxylic acid anhydride containing polymer, e.g., EMA, in a dry organic solvent such as toluene or dimethylformamide and with the optional use of an acidic or basic catalyst such as p-toluenesulfonic acid or sodium alkoxide. The resulting product contains ester groups, carboxylic acid groups and anhydride groups, the respective numbers of which are determined by the quantity of aminoalcohol used in the reaction compared to the amount of polymer employed and, in some cases, by the temperature at which the reaction is carried out.

Suitable blocking and unblocking of the amine moiety of the reactant employed in preparing amides, esters or imides may be effected when required. Residual, nonmodified, polymer units may optionally be converted to neutral groups or units by attachment to the polymer molecule of compounds including alkylamines, aminoalcohols, and alcohols.

Alternatively, the cationic character of the polymer can be provided through incorporation of monomers which impart a basic or cationic character such as C-vinyl pyridines, vinyl amine, the several amino-substituted vinyl benzenes (or toluenes, etc.), amine-bearing acrylates (or methacrylates, etc.), vinyl imidazole, etc.

The invention will be understood more fully by reference to the following specific examples. It is understood that the examples are presented for the purpose of illustration only and are not intended as a limitation of the invention.

EXAMPLE 1

To determine the effect of polymers of the present invention in lowering blood cholesterol levels the following test was conducted.

A group of 144 Columbian male chicks (one day old) was divided in 12 equal sub-groups. Each sub-group of 12 chicks was fed a basal diet and the supplement shown in Table 1 for a three-week period. Throughout the test period water was supplied ad libitum. The basal diet employed was designed to raise the level of blood cholesterol in the chicks to which it was fed. On conclusion of the feeding period the chicks were sacrificed and plasma cholesterol level was determined by the general procedure described in Chin. Chim. Acta. 10 381–84 (1964) by Levine and Zak. Fecal cholesterol and fecal lipid were also determined. In the test the copolymers of diets 2–10 and 12 are linear and the copolymer of diet 11 is crosslinked. The results are set forth in Table 1:

| Basal Diet | |
|---|---|
| Ingredient | % by Weight |
| Soybean Meal | 25.00 |
| Whole Egg (Powder) | 25.00 |
| Vitamin Supplement | 0.40 |
| Choline Chloride | 0.14 |
| Iodized Salt | 0.05 |
| Delamix | 0.10 |
| Dicalcium Phosphate | 2.00 |
| Calcium Carbonate | 1.00 |
| Vitamin A (10,000 u/g) | 0.10 |
| Vitamin D(1,500 u/g) | 0.008 |
| Alpha Cel | 3.00 |
| Cerelose | 42.752 |

The results of this test show that the polyelectrolyte polymers of the present invention are effective in lowering blood cholesterol and in increasing fat excretion.

TABLE 1

| Diet | Polymer | Level in Feed % by weight | Plasma Cholesterol mg/100 ml | Fecal Cholesterol % dry weight | Fecal Lipid % dry weight |
|---|---|---|---|---|---|
| 1 | None (Control) | — | 213 | 0.75 | 4.70 |
| 2 | Octadecene-1/Maleic Anhydride Copolymer | 0.5 | 183 | 1.06 | 6.9 |
| 3 | Octadecene-1/Maleic Anhydride Copolymer | 1.0 | 150 | 1.32 | 9.28 |
| 4 | Octadecene-1/Maleic Anhydride Copolymer | 2.0 | 125 | 1.38 | 7.74 |
| 5 | Octadecene-1/Maleic Anhydride Copolymer | 3.0 | 107 | 1.43 | 10.29 |
| 6 | N,N-Dimethylaminopropyl-imide of Octadecene-1/Maleic Anhydride Copolmer | 3.0 | 114 | 1.58 | 24.7 |
| 7 | Partial lauryl ester of ethylene/Maleic Anhydride Copolymer | 3.0 | 149 | 0.64 | 7.4 |
| 8 | Vinyloctadecyl ether/Maleic Anhydride Copolymer | 3.0 | 141 | 1.06 | 8.1 |
| 9 | Stearyl methacrylate/Methacrylamide Copolymer | 3.0 | 136 | 1.32 | 9.8 |
| 10 | Stearyl methacrylate/N,N-dimethylamino ethyl methacrylate copolymer | 3.0 | 120 | 1.56 | 22.4 |
| 11 | N,N-Dimethylaminopropylimide of styrene/maleic anhydride copolymer | 3.0 | 107 | 1.53 | 20.3 |
| 12 | Octene-1/maleic Anhydride Copolymer | 3.0 | 147 | 1.40 | 12.21 |

EXAMPLE 2

A group of 36 Vantress-Arbor Acre male chicks (one day old) was divided into three equal subgroups. Each subgroup of 12 chicks was fed the Basal Diet of Example 1 and 3.0% of the supplement shown in Table 2 for a three week period. Throughout the test period water was supplied ad libitum. On conclusion of the feeding period the chicks were sacrificed and plasma cholesterol level was determined by the procedure referred to in Example 1. In the test the copolymers of diet 14 and 15 were crosslinked. The results are set forth in Table 2.

TABLE 2

| DIET | POLYMER | PLASMA CHOLESTEROL mg/100 ml |
| --- | --- | --- |
| 13 | None | 290.5 |
| 14 | Ethylene/maleic anhydride | 204.8 |
| 15 | Ethylene/maleic anhydride hydrolyzed | 192.8 |

EXAMPLE 3

The procedure of Example 2 was repeated. The polymers used and the results obtained are given in Table 3.

TABLE 3

| DIET | POLYMER | PLASMA CHOLESTEROL mg/100 ml |
| --- | --- | --- |
| 16 | None | 309 |
| 17 | Ethylene/maleic anhydride (crosslinked) | 275 |
| 18 | Ethylene/maleic anhydride calcium salt (crosslinked) | 255 |

EXAMPLE 4

The procedure of Example 1 is repeated in all essential details with the exception that the polymer is polymaleic anhydride to lower the blood cholesterol level of the chicks.

EXAMPLE 5

The procedure of Example 1 is repeated in all essential details with the exception that the polymer is polyacrylic anhydride to lower the blood cholesterol level of the chicks.

EXAMPLE 6

The procedure of Example 1 is repeated in all essential details with the exception that the polymer is polyacrylic acid to lower the blood cholesterol of the chicks.

EXAMPLE 7

The procedure of Example 1 is repeated in all essential details with the exception that the polymer is polymethacrylic acid to lower the blood cholesterol level of the chicks.

EXAMPLE 8

Cattle having a high level of blood cholesterol are fed a daily ration containing from 0.01 to 5.0% of octadecane-1/maleic anhydride and the level of their blood cholesterol is lowered.

EXAMPLE 9

Heavy weight Hampshire hogs having a high level of blood cholesterol are fed a daily ration containing from 0.01 to 3.0% of N,N-dimethylaminopropylimide of octadecene-1/maleic anhydride copolymer and the level of their blood cholesterol is lowered.

EXAMPLE 10

Aged chimpanzees having a high level of blood cholesterol are fed a daily ration containing from 0.05 to 1.0% of octadecene-1/maleic anhydride copolymer and the level of their blood cholesterol is lowered.

EXAMPLE 11

This example shows the effectiveness of octadecene-1/maleic anhydride (substantially equimolar copolymer) in the method of the present invention. Twenty-four New Zealand white rabbits weighing an average of 2600 grams each were divided into three groups of equal number. The rabbits were fed ad libitum for 5 weeks a low cholesterol diet. The first group (control) was fed Purina Rabbit Chow brand rabbit feed supplemented with 2% animal tallow and 1% cellulose. The second group was fed the identical feed as the control with the exception that 1% octadecene-maleic anhydride was substituted for the 1% cellulose. The third group was fed the identical feed as the control with the exception that 1% CHOLESTYRAMINE, a crosslinked divinyl-benzene-polystyrene ion exchange resin containing quanternary ammonium groups was substituted for the 1% cellulose. On completion of the five week feeding period the animals were sacrificed and the following measurements were made: (1) plasma cholesterol, (2) plasma triglyceride, (3) liver cholesterol, and (4) liver fat. The measurements were averaged and are presented in Table 4. These results when considered as a whole indicate that higher a-olefin/maleic anhydride copolymers are effective in lowering blood lipids, i.e., in the treatment of hypercholesterolemia.

EXAMPLE 12

This example shows the effectiveness of octadecene-1/maleic anhydride (substantially equimolar copolymer) in the method of the present invention. Forty New Zealand white rabbits weighing an average of 2600 grams each were divided into five groups of equal number. The groups were fed ad libitum for five weeks a high cholesterol diet. The first group (control) was fed Purina Rabbit Chow brand rabbit feed supplemented with 2% animal tallow, 1% cellulose and 0.2% cholesterol. The second group was fed the identical feed as the control with the exception that 0.5% octadecene-maleic anhydride was substituted for 0.5% of the cellulose. The third group was fed the identical feed as the control with the exception that 1% octadecene maleic anhydride was substituted for the 1% cellulose. The fourth group was fed the identical feed as the control with the exception that 0.5% CHOLESTYRAMINE was substituted for 0.5% of the cellulose. The fifth group was fed the identical feed as the control with the exception that 1% CHOLESTYRAMINE was substituted for the 1% cellulose. Feces were collected during the final day of the test. On completion of the five-week feeding period the animals were sacrificed. The measurements performed in Example 11 above were carried out. Fecal fat was also measured. The measurements were averaged and are presented in Table 5.

EXAMPLE 13

This example shows the effectiveness of polymers useful in the present invention. Four hundred and sixty-eight one-day old chicks (Vantress-Arbor Acre Cockerels) were divided into thirteen groups of equal number. Each group of chicks was fed ad libitum for 21 days a high cholesterol diet of soy bean meal, whole egg powder, minerals and vitamins. Cholesterol lowering additive in the amount indicated in Table 6 was added to the diet of groups 2–13. Group 1 served as a control. Feces were collected for a 24-hour period between days 19 and 20. On completion of the 21-day test the birds were sacrificed and the following measurements were made: (1) plasma cholesterol, (2) liver cholesterol, and (3) liver fat. The measurements were averaged and are presented in Table 6.

EXAMPLE 14

This example shows the effectiveness of representative members of (1) a group of polymers which are copolymers of higher a-olefins (10–22 carbon atoms or more) and maleic acid or maleic anhydride and (2) a group of polymers which are copolymers of higher alkyl vinyl ethers (10–22 carbon atoms or more) and maleic acid or maleic anhydride. The maleic acid copolymers were prepared by hydrolysis of the corresponding maleic anhydride copolymers in 5% acetic acid in water at 50° C. for 24 hours followed by freeze drying.

Thirty-six female rabbits (1.5–2.0 kilograms each) were placed in individual cages. The rabbits were randomly divided into 12 groups (3 animals per group) for feeding purposes and fed ad libitum for three weeks high cholesterol diets. The first group (control) was fed a basal diet designed to induce hypercholesterolemia. The die consisted of Purina Rabbit Chow brand rabbit feed supplemented with 2% animal tallow, 0.2% cholesterol and 1% cellulose. The other 11 groups were fed the identical basal diet as the control group with the exception that 1% of a copolymer useful in the present invention was substituted for the 1% cellulose. On completion of the three-week feeding period the animals were weighed and blood samples were taken. The samples were analyzed for cholesterol (Technicon autoanalyzer). At the beginning of the test, a blood sample was taken from each animal (heart puncture) and analyzed for cholesterol. All results are presented in Table 7. The effectiveness of a tested compound is shown by comparing the final plasma cholesterol of the animals treated with the compound with the final plasma cholesterol of the control animals.

EXAMPLE 15

Three baboons were fed a high cholesterol diet for eight weeks. At the beginning of the fourth week of feeding, octadecene-1/maleic anhydride copolymer (0.5% by weight of the total diet) was added to the diet of two of the baboons and equal CHOLESTRYRAMINE, a crosslinked divinylbenzene-polystyrene ion exchange resin containing quaternary ammonium groups was added to the diet of the third baboon. In each of the three animals the blood cholesterol level was found to be lower at the end of the eighth week than at the end of the third week with the blood cholesterol level at the end of the eighth week being lower in the two animals fed the diet containing octadecene/maleic anhydride copolymer than in the animal fed the diet of CHOLESTRYRAMINE.

Representative formulations embodying polymers within the scope of the present invention are:

TABLET FORMULATION

The following formulation provides for the manufacture of 1,000 tablets:

| | | GRAMS |
|---|---|---|
| (1) | Octadecene-1/maleic anhydride copolymer | 25 |
| (2) | Lactose | 181 |
| (3) | Corn Starch | 92 |
| (4) | Magnesium Stearate | 2 |

Thoroughly granulate a mixture of 72 grams of cornstarch and the lactose with a paste prepared by dissolving 20 grams of cornstarch in 100 ml of hot distilled water. Dry the resulting granulation at 40°–45° C. and pass it through a No. 16-mesh screen. To the dried, screened granulation add a blended mixture of the active ingredient (1) and the magnesium stearate. Thoroughly blend and then press into tablets of 300 mg. each.

CAPSULE FORMULATION

The following formulation provides for the manufacture of 1,000 capsules:

| | | GRAMS |
|---|---|---|
| (1) | N,N-dimethylaminopropylimide of octadecene-1/maleic anhydride copolymer | 25 |
| (2) | Lactose | 274 |
| (3) | Magnesium Stearate | 2 |

Mix active ingredient (1) with the lactose and blend in the magnesium stearate. Fill hard gelatin capsules with 300 mg. each of the blended mixture to produce capsules containing the active ingredient.

While the invention has been described with reference to particular embodiments thereof, it will be appreciated that modifications and variations are possible without departing from the invention.

TABLE 4

| | | PLASMA | | LIVER | |
|---|---|---|---|---|---|
| | | Cholesterol *mg % | Triglyceride *mg % | Cholesterol % Of wet weight | Fat |
| Group 1 | (Control) | 52 | 82 | .38 | 6.89 |
| Group 2 | (1% Octadecene-maleic anhydride) | 43 | 87 | .36 | 5.12 |
| Group 3 | (1% CHOLESTYRAMINE) | 74 | 110 | .39 | 5.69 |

*mg per 100 cc plasma.

TABLE 5

| | | PLASMA | | LIVER | | FECES |
|---|---|---|---|---|---|---|
| | | Cholesterol *mg % | Triglyceride *mg % | Cholesterol % of wet weight | Fat | Fat % of dry wt. |
| Group 1 | (Control) | 672 | 106 | .92 | 7.80 | 4.51 |
| Group 2 | (0.5% Octadecene-maleic anhydride) | 186 | 113 | .47 | 5.98 | 6.03 |
| Group 3 | (1.0% Octadecene-maleic anhydride) | 89 | 56 | .41 | 5.80 | 6.29 |
| Group 4 | (0.5% CHOLESTYRAMINE) | 356 | 68 | .79 | 7.36 | 7.12 |

TABLE 5-continued

|  | PLASMA | | LIVER | | FECES |
|---|---|---|---|---|---|
|  | Cholesterol *mg % | Triglyceride *mg % | Cholesterol % of wet weight | Fat % of wet weight | Fat % of dry wt. |
| Group 5 (1.0% CHOLESTYRAMINE) | 310 | 105 | .74 | 7.18 | 6.04 |

*mg per 100 cc of plasma.

TABLE 6

|  |  | Weight Grams | Feed Consumed Grams | Plasma Cholesterol mg % | Liver Cholesterol % wet wt. | Liver Fat % wet wt. | Excreta Cholesterol % dry wt. | Excreta Fat % dry wt. |
|---|---|---|---|---|---|---|---|---|
| Group 1 | (control) | 328 | 472 | 257 | 2.58 | 10.7 | 0.46 | 6.2 |
| Group 2 | (Octadecene-maleic anhydride) (0.6%) | 360 | 483 | 250 | 1.26 | 8.9 | 0.97 | 6.3 |
| Group 3 | (Octadecene-maleic anhydride) (1.2%) | 338 | 509 | 236 | 0.57 | 7.6 | 1.03 | 10.1 |
| Group 4 | (CHOLESTYRAMINE) (0.6%) | 364 | 480 | 181 | 0.50 | 7.6 | 1.09 | 11.9 |
| Group 5 | (CHOLESTYRAMINE) (1.2%) | 331 | 428 | 154 | 0.45 | 7.7 | 1.12 | 11.4 |
| Group 6 | (Octadecene-maleic anhydride dimethylaminopropylimide-100% derivative) (0.6%) | 354 | 491 | 226 | 0.89 | 8.2 | 0.83 | 11.2 |
| Group 7 | (Octadecene-maleic anhydride dimethylaminopropylimide-67% derivative) (0.6%) | 315 | 456 | 258 | — | — | 0.65 | 12.8 |
| Group 8 | (Stearylmethacrylate/dimethyl-aminoethylmethacrylate) (0.6%) | 233 | 395 | 206 | 0.57 | 7.2 | 1.01 | 17.3 |
| Group 9 | (Stearylmethacrylate/dimethyl-aminoethylmethacrylate) (0.6%) | 370 | 501 | 262 | — | — | 0.80 | 14.1 |
| Group 10 | (Vinyloctadecyl ether/maleic anhydride) (0.6%) | 361 | 463 | 242 | 0.87 | 7.9 | 1.11 | 12.0 |
| Group 11 | (Vinyloctadecyl ether/maleic anhydride) (0.6%) | 360 | 514 | 298 | — | — | 0.97 | 9.5 |
| Group 12 | (Stearyl methacrylate/methacrylic acid) (0.6%) | 358 | 439 | 282 | — | — | 0.73 | 9.5 |
| Group 13 | (Stearyl methacrylate/methacrylic acid) (0.6%) | 369 | 455 | 274 | — | — | 0.84 | 9.5 |

TABLE 7

|  | Polymer | Weight Gain in Grams For 3 Week Period (Average) | Plasma Cholesterol Initial mg.%* (Average) | Plasma Cholesterol Final mg.%* (Average) |
|---|---|---|---|---|
| 1 | (Control) | 546 | 53 | 377 |
| 2 | Octadecene/maleic anhydride (2:3) (1) | 461 | 51 | 117 |
| 3 | Octadecene/maleic acid (2:3) | 487 | 123 | 84 |
| 4 | Octadecene/maleic anhydride (1:1) | 436[2] | 147[2] | 70[2] |
| 5 | Octadecene/maleic acid (1:1) | 288 | 61 | 112 |
| 6 | Decene/maleic anhydride (1:1) | 228 | 67 | 153 |
| 7 | Decene/maleic acid (1:1) | 320 | 78 | 117 |
| 8 | Octadecyl vinyl ether/maleic anhydride | 460 | 91 | 162 |
| 9 | Octadecyl vinyl ether/maleic acid | 279[3] | 64[3] | 344[3] |
| 10 | Dodecyl vinyl ether/maleic anhydride (1:1) | 365 | 70 | 260 |
| 11 | Dodecyl vinyl ether/maleic acid (1:1) | 538 | 60 | 103 |
| 12 | Hexene/maleic anhydride (1:1) | 670 | 60[4] | 472[4] |

*mg. per 100 cc of plasma
[1] mole ratio of a-olefin to anhydride
[2] 1 animal died of diarrhea during test (average of 2 animals)
[3] 1 animal suffered severe weight loss due to diarrhea during test (average of 2 animals)
[4] 2 animals suffered severe weight loss due to diarrhea during test

What we claim is:

1. A method of controlling blood cholesterol levels in a living animal body in need of such control which comprises orally administering to said animal body a pharmaceutically effective amount of material comprising a lipophilic polymer effective for such purpose and having recurring units of copolymer of (1) alpha-olefin of at least 10 carbon atoms selected from alkoxy-olefins, alkylcarboxyl olefins, or mixtures thereof, with (2) unsaturated carboxylic acids, or anhydrides, or the amides, esters, imides or salts thereof, or mixtures of the foregoing, said copolymer having a molecular weight in the range of from about 1,000 to about 1,000,000, and said pharmaceutically effective amount being sufficient to achieve such control.

2. A method for lowering the blood cholesterol level in a living animal in need thereof to a cholesterol value below that which the animal would have in the absence of treatment comprising orally administering to said animal an effective blood cholesterol lowering amount of a lipophilic copolymer of (1) alpha-olefin of at least 10 carbon atoms selected from alkoxy-olefins, alkylcarboxyl olefins, or mixtures thereof, with (2) unsaturated carboxylic acids, or anhydrides, or the amides, esters, imides or salts thereof, or mixtures of the foregoing, said copolymer having a molecular weight in the range of from about 1,000 to 1,000,000.

3. The method of claim 2 wherein the copolymer is octadecyl vinyl ether/maleic anhydride.

4. The method of claim 2 wherein the copolymer is dodecyl vinyl ether/maleic anhydride.

5. The method of claim 2 wherein the copolymer is octadecyl vinyl ether/maleic acid.

6. The method of claim 2 in which the copolymer is dodecyl vinyl ether/maleic acid.

7. A method of lowering the level of blood cholesterol in a living animal body in which a state of hypercholesterolemia exists which comprises orally administering to said animal body a pharmaceutically effective amount of a copolymer of (a) a higher alkyl vinyl ether having at least 10 and up to 30 carbon atoms and (b) maleic acid or anhydride, said copolymer having a molecular weight in the range of from about 1,000 to about 1,000,000 said pharmaceutically effective amount being sufficient to lower the level of blood cholesterol in the said living animal body.

8. The method of claim 1 in which the acid is methacrylic acid.

9. A method of controlling blood cholesterol levels in a living animal body in need of such control which comprises orally administering to said animal body a pharmaceutically effective amount of material comprising a lipophilic polymer effective for such purpose and having recurring units of copolymer of olefinic hydrocarbons of at least 10 carbon atoms with unsaturated monocarboxylic acids, or anhydrides, or the amides, esters, imides, or salts thereof, or mixtures of the foregoing, said copolymer having a molecular weight in the range of from about 1,000 to about 1,000,000, and said pharmaceutically effective amount being sufficient to achieve such control.

10. A pharmaceutical composition effective for controlling blood cholesterol levels in a living animal body comprising an effective amount of material comprising a lipophilic copolymer effective for such purpose and having recurring units of copolymer of (1) alpha-olefin of at least 10 carbon atoms, selected from alkoxy-olefins, alkylcarboxyl olefins, or mixtures thereof, with (2) unsaturated carboxylic acids, or anhydrides, or the amides, esters, imides, or salts thereof, or mixtures of the foregoing, said copolymer having a molecular weight in the range of from about 1,000 to about 1,000,000 and said pharmaceutically effective amount being sufficient to achieve such control, and a pharmaceutically acceptable carrier.

11. A pharmaceutical composition effective in lowering blood cholesterol and suitable for oral administration comprising an effective cholesterol lowering amount of a copolymer of (a) alkyl vinyl ether having at least 10 carbon atoms and (b) maleic acid or anhydride, said copolymer having a molecular weight in the range of from about 1,000 to about 1,000,000 and a pharmaceutically acceptable carrier therefor.

12. A pharmaceutical composition effective for lowering blood cholesterol comprising the polymer as defined in claim 9 and a pharmaceutically acceptable carrier therefor.

13. The composition of claim 10 wherein the copolymer is octadecyl vinyl ether/maleic anhydride.

14. The composition of claim 10 wherein the copolymer is dodecyl vinyl ether/maleic anhydride.

15. The composition of claim 10 wherein the copolymer is octadecyl vinyl ether/maleic acid.

16. The composition of claim 10 in which the copolymer is dodecyl vinyl ether/maleic acid.

17. The composition of claim 10 in unit dosage form.

18. An animal nutrient composition effective for controlling blood cholesterol levels in a living animal body comprising an effective amount of material comprising nutrient ration and a lipophilic polymer effective for such purpose and having recurring units of copolymer of (1) alpha-olefin of at least 10 carbon atoms selected from alkoxy-olefins, alkyl-carboxyl olefins, or mixtures thereof, with (2) unsaturated carboxylic acids, or anhydrides, or the amides, esters, imides, or salts thereof, or mixtures of the foregoing, said copolymer having a molecular weight in the range of from about 1,000 to about 1,000,000, and said pharmaceutically effective amount being sufficient to achieve such control.

19. An animal feed composition comprising a nutrient ration and a cholesterol-lowering amount of a copolymer of (a) alkyl vinyl ether having at least 10 and up to about 22 carbon atoms and (b) maleic acid or anhydride, said copolymer having a molecular weight in the range of from about 1,000 to about 1,000,000 said cholesterol-lowering amount being sufficient to lower the level of blood cholesterol in the said living animal body.

20. The composition of claim 19 wherein the copolymer is octadecyl vinyl ether/maleic anhydride.

21. The composition of claim 19 wherein the copolymer is dodecyl vinyl ether/maleic anhydride.

22. The composition of claim 19 wherein the copolymer is octadecyl vinyl ether/maleic acid.

23. The composition of claim 19 in which the copolymer is dodecyl vinyl ether/maleic acid.

* * * * *